United States Patent [19]

Yamamoto et al.

[11] Patent Number: 5,061,452
[45] Date of Patent: Oct. 29, 1991

[54] CASSETTE FOR PATHOLOGICAL TISSUE EXAMINATION

[75] Inventors: Tadashi Yamamoto, Amagasaki; Takuya Murazumi, Ashiya, both of Japan

[73] Assignee: Murazumi Industrial Co., Ltd., Himeji, Japan

[21] Appl. No.: 256,945

[22] Filed: Oct. 13, 1988

[30] Foreign Application Priority Data

Oct. 14, 1987 [JP] Japan ............................ 62-157173[U]

[51] Int. Cl.$^5$ ............................................. B01L 11/00
[52] U.S. Cl. ................................... 422/101; 422/102; 422/292; 435/301; 425/117; 206/0.5; 206/473; 220/504; 220/526
[58] Field of Search .................. 422/99, 101, 102, 104, 422/292, 300, 302; 435/1, 283, 284, 298, 300, 301; 425/117; 220/22, 23, 23.8, 23.2, 500, 504, 526; 206/0.5, 205, 210, 473, 483, 490

[56] References Cited

U.S. PATENT DOCUMENTS

| | | | |
|---|---|---|---|
| 2,783,180 | 2/1957 | Whitehead | 206/0.5 |
| 3,128,902 | 4/1964 | Barnum | 435/284 |
| 3,168,100 | 2/1965 | Rich | 422/300 |
| 4,220,252 | 9/1980 | Beall et al. | 220/307 |
| 4,421,246 | 12/1983 | Schultz et al. | 206/205 |
| 4,541,992 | 9/1985 | Jerge et al. | 422/300 |
| 4,557,903 | 12/1985 | McCormick | 422/102 |
| 4,801,553 | 1/1989 | Owen et al. | 422/102 |

Primary Examiner—David L. Lacey
Assistant Examiner—William H. Beisner
Attorney, Agent, or Firm—Armstrong, Nikaido, Marmelstein, Kubovcik & Murray

[57] ABSTRACT

This invention provides a cassette for pathological tissue examination which consists of a container proper and a lid thereof engageable therewith and detachable therefrom both made of a chemical-resistant synthetic resin, wherein the aforementioned container proper has a plurality of sample chambers independent and separated from one another when the container proper is closed, a large number of small through-holes are made in the bottom of the container proper having the aforementioned sample chambers formed therein and the lid, and either or both of the container proper and the lid is/are provided with a recording space in which the name, serial No. et cetera of the examinee can be written or otherwise recorded. The cassette of the invention features easy taking-in and taking-out of samples and treatment thereof with alcohol et cetera, ensures prevention of primitive errors such as mistaking the examinees or the places the particular samples were taken from, excellent in workability and contributes to improvement in efficiency as well as reliability of such examination.

7 Claims, 4 Drawing Sheets

CASSETTE FOR PATHOLOGICAL TISSUE EXAMINATION

BACKGROUND OF THE INVENTION

1. Field of the Invention

The present invention relates to a cassette for pathological tissue examination and, more particularly, to such cassette which can improve the workability or efficiency of making preparations for microscopy including taking-in of a medical sample such as of a living body tissue and chemical treatment thereof at the same time helping improve the efficiency and reliability of such examination.

2. Description of the Prior Art

Today, in the diagnosis of cancer et cetera the method of histologically examining tissue samples taken from a living body, the so-called biopsy is widely used. In such a biopsy, for example, a sample of approximately 0.5–5 mm of the object living body tissue is taken, rinsed with water, treated with xylene after dehydration with alcohol and then embedded in paraffin, and it is sliced to make preparations for microscopic examination.

Hitherto, as container for such a tissue sample, a cloth bag made of a chemical-resistant fiber, some 4.5 cm long and 6.5 cm wide and approximately 0.2 mm in mesh size was used, a tissue sample was taken in and the mouth of the bag was closed before the aforementioned treatment was proceeded with. This method is, however, extremely poor in workability and, especially when a fraction of the sample is in a corner or the bottom of the bag, it is by no means easy to take it out using a pair of pincers. Further, while in biopsy it is usually the case that, even if the object organ is one, several samples of living body tissue are taken from different parts of the organ, the method described above using a mesh bag lacks marking means, hence when several samples are taken into a bag, they are indistinguishable, and the method being used in practice nowadays is to take each sample into one bag together with a card or the like with the name et cetera of the examinee written thereon, being thus dreadfully inefficient. Also, in such a method, if the aforementioned card or the like should come out of the bag, the examinee is no longer identifiable and other necessary data, if any, are lost, this greatly interferes with the reliability of the examination, and, worse, a separate container having through-holes therein, the so-called cassette, is required when the living body tissue is embedded in paraffin for making preparations for microscopy. There are also many other problems such as the possibility of the taken sample being deformed when the bag is subjected to a even a small force.

SUMMARY OF THE INVENTION

It is a primary object of the present invention to provide a cassette for pathological tissue examination for making it easy to insert and remove samples and well permeable to alcohol and paraffin.

Another object of the present invention is to provide a cassette for pathological tissue examination enabling simultaneous treatment of a plurality of samples.

A still another object of the present invention is to provide a cassette for pathological tissue examination to ensure against primitive, yet grave errors such as misidentifying the examinees.

Further objects and advantages of the present invention will become apparent from reading of the detailed description of the invention below.

After extensive and intensive studies for accomplishing the above objects the present inventors have succeeded in inventing a cassette for pathological tissue examination which consists of a container proper and a lid thereof engageable therewith and detachable therefrom both made of a chemical-resistant synthetic resin, wherein the aforementioned container proper has a plurality of sample chambers independent and separated from one another when the container proper is closed, a large number of small through-holes are made in the bottom of the container proper having the aforementioned sample chambers formed therein and the lid, and either or both of the container proper and the lid is/are provided with a recording space in which the name, serial No. et cetera of the examinee can be written or otherwise recorded.

DETAILED DESCRIPTION OF THE INVENTION

The present invention relates to a cassette for pathological tissue examination which consists of a container proper and a lid thereof engageable therewith and detachable therefrom both made of a chemical-resistant synthetic resin, wherein the aforementioned container proper has a plurality of sample chambers independent and separated from one another when the container proper is closed, a large number of small through-holes are made in the bottom of the container proper having the aforementioned sample chambers formed therein and the lid, and either or both of the container proper and the lid is/are provided with a recording space in which the name, serial No. et cetera of the examinee can be written or otherwise recorded.

Figure 1:
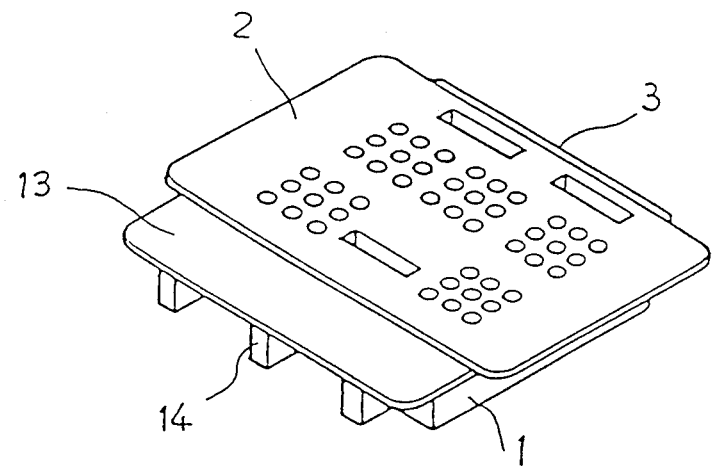
FIG. 1 is a schematic view showing an embodiment of the present invention.
Figure 2:
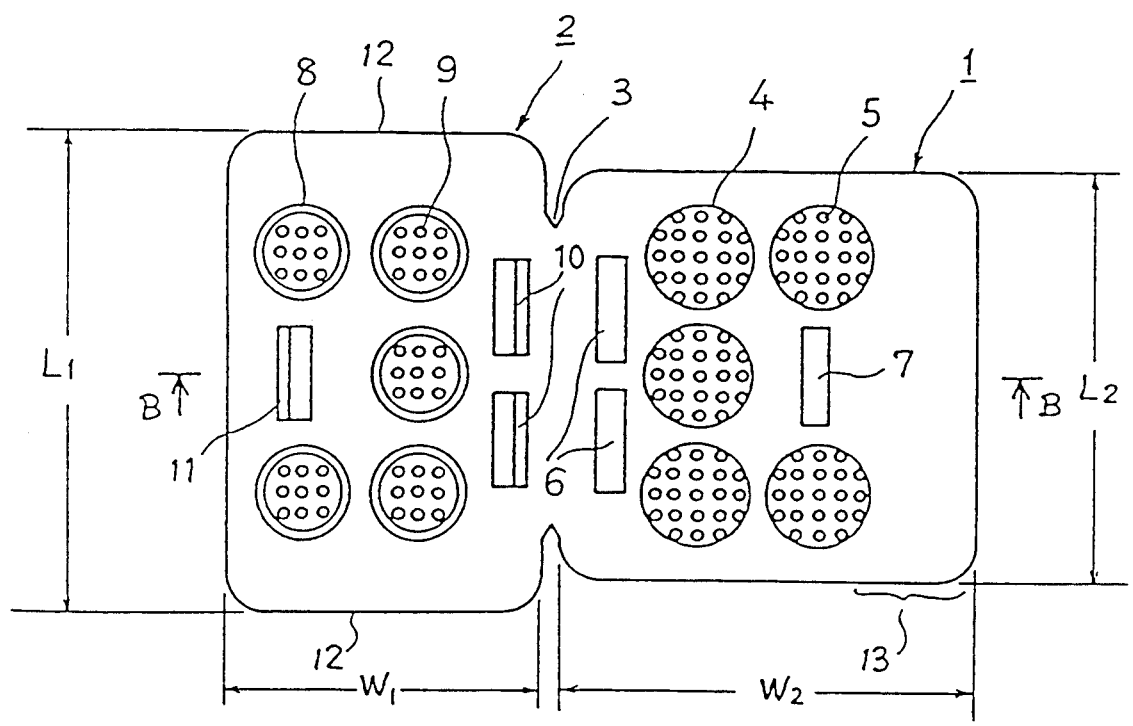
FIG. 2 is a plan view thereof with the lid opened.
Figure 3:
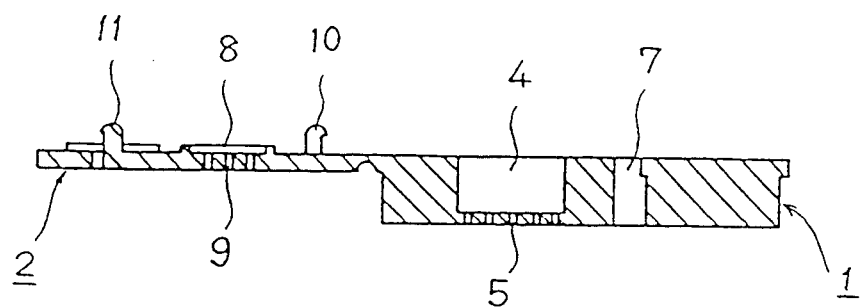
FIG. 3 is a sectional view taken along the line B—B in FIG. 2.
Figure 4:
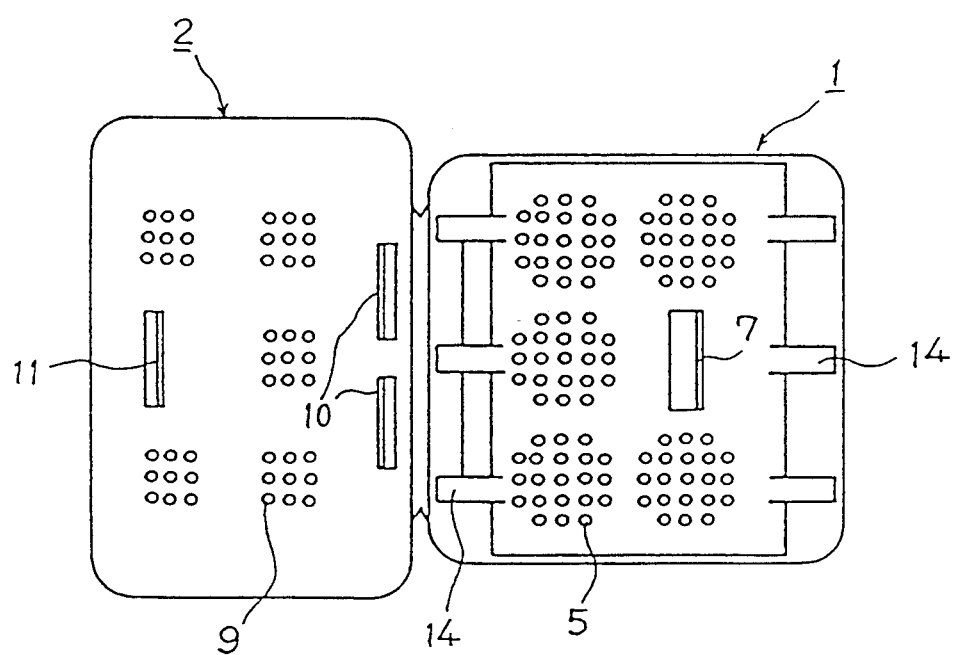
FIG. 4 is a bottom view corresponding to FIG. 2.

Of the drawings showing embodiments of the present invention, FIG. 1 is a schematic view of the cassette of the invention, FIG. 2 is a plan view thereof with its lid opened, FIG. 3 is a sectional view taken along the line B—B in FIG. 2 and FIG. 4 is a bottom view corresponding to FIG. 2.

Referring to these figures, the cassette of the present invention consists of a container proper (1) and a lid (2) and these are connected by a hinge (3). The aforementioned container proper (1) has formed therein a plurality (5 in the figure) of sample chambers (4) and in the bottom of the sample chambers (4) are made a large number of small through-holes (5). Near both ends of the container proper (1) there are provided sunken parts (6) and (7) and on the side opposing the lid of the container proper (1) is provided a recording space (13) for writing or otherwise recording the name, serial No. et cetera of the examinee.

Meanwhile, on the back of the aforementioned lid (2) there are provided the same number and size of projected rims (8) to match the sample chambers (4) of the aforementioned container proper (in the opposing positions), and there are made a large number of small through-holes (9) inside these projected rims (8). Near both ends of the lid (2) there are provided projections (10) and (11). It is so designed that the vertical length ($L_1$) of the lid (2) is slightly larger than the length of the container proper ($L_2$) so that, when the container is closed, the lid (2) projects by a proper dimension beyond the ends of the container proper (1) so that holders (12) for opening the lid (2) are provided, and that the lid's horizontal length ($W_1$) is smaller than the length ($W_2$) of the container proper so that the aforementioned recording space (13) is not covered.

The container proper (1) and the lid (2) as described above are mated when the hinge (3) is bent inward so that the projections (10) and (11) of the lid (2) fit in the sunken parts (6) and (7) of the container proper (1) and the projected rims (8) of the lid (2) fit in the sample chambers (4) of the container proper (1) respectively for 5 independent and tightly sealed chambers to be formed thereby. To open the container, the holder (12) may be held with fingers and the lid (2) is lifted to break the aforementioned engagement.

According to the present invention, the container proper (1) and the lid (2) are both made of a chemical-resistant synthetic resin. As chemical-resistant synthetic resin, there may be included, for example, polyacetal resin, polyamide resin, polycarbonate resin, polyester resin and fluorocarbon resin. As to the number of the sample chambers (4), there is no particular limitation, but 3–9 is considered proper when the preferred overall size of the cassette of the present invention is approximately 20–30 mm in length, 30–40 mm in width and 5–8 mm in height with the ease in handling taken into consideration. If this number is less than 3, the sample-holding capacity is supposed to be insufficient, while, if it is more than 9, the size of each sample chamber is bound to be too small, this possibly interfering with manipulation by the use of pincers. There is no particular limitation with regard to the shape of the sample chamber, either, but it may preferably be cylindrical, for this precludes the possibility of sample in a corner being inaccessible and also facilitate manipulation with pincers. The size of small through-holes (5) and (9) may preferably be in a range of 0.2–0.7 mm or so. If it is too small, the permeability to alcohol, xylene or liquid paraffin described below becomes insufficient, while if it is too large, there is a risk of tiny samples dropping through such through-holes. Also, it is preferred to have the small through-holes (5) tapered to be narrower toward the chamber interior, and the small through-holes (9) tapered to be broader toward the chamber interior. This not only prevents the small through-holes being clogged with the sample but also improves their permeability to alcohol, paraffin or the like.

In the aforementioned figure there are provided on the back of the container proper (1) paraffin engaging and reinforcing parts (14) are provided. This construction not only increasing the engaging force between the underside of the container proper and paraffin but also is effective for reinforcing the container proper (1), hence the wall thickness of the container proper can be made smaller, the permeability to alcohol, xylene and paraffin can be improved and, as will be described later, reinforcing effect is exhibited when a cassette block is sliced by the use of a microtome.

Figure 5:
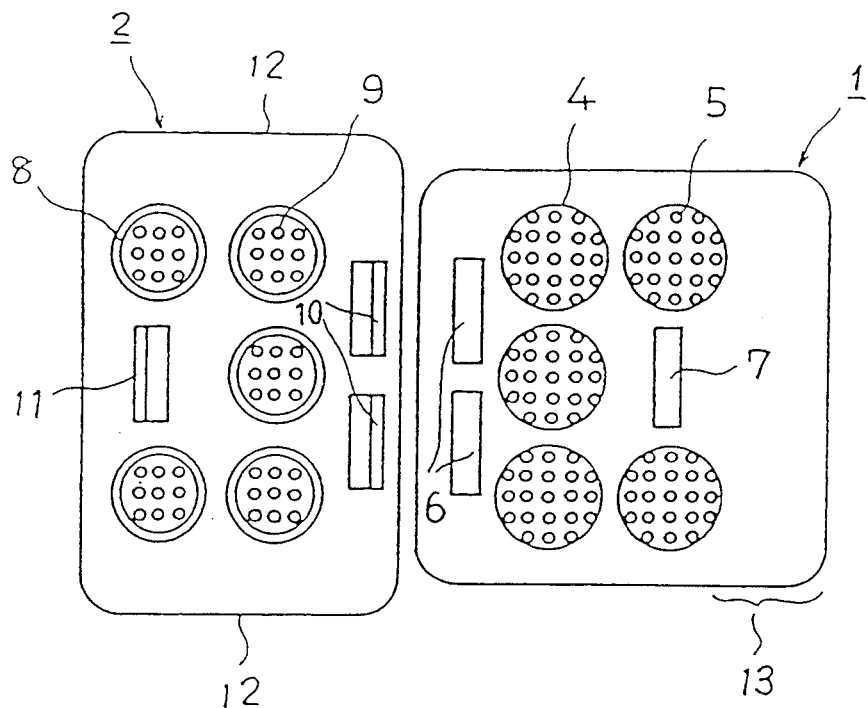
FIG. 5 is a plan view showing another embodiment of the present invention.

FIG. 5 is a plan view showing another embodiment of the present invention, and in this embodiment the container proper (1) is separated from the lid (2).

Figure 6:
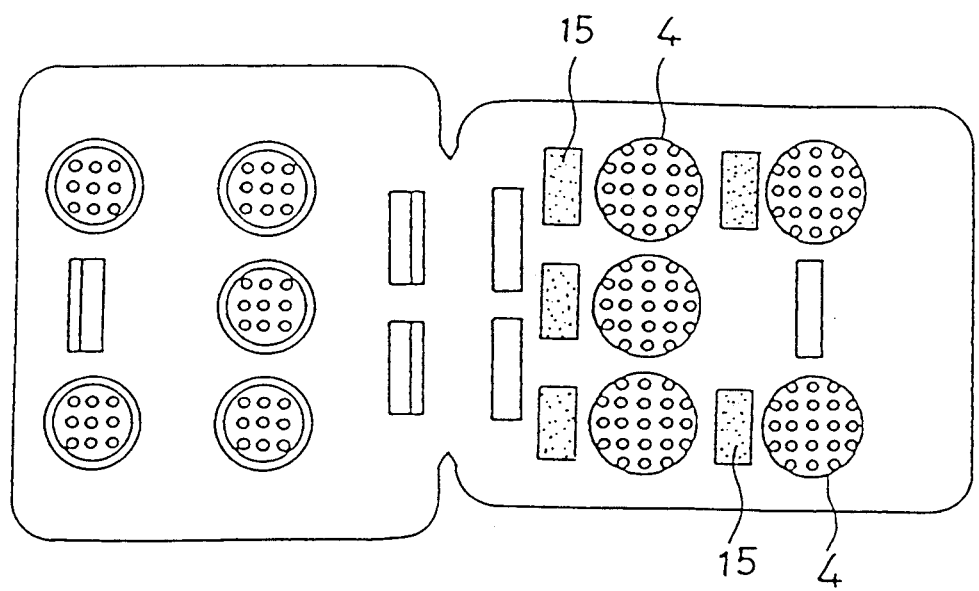
FIG. 6 is a plan view showing still another embodiment of the present invention.

FIG. 6 shows a still another embodiment of the present invention, and here a marking part (15) is provided near each sample chamber (4) of the container proper (1). This marking part is pear skin-finished to allow writing with a ball-point pen or the like and is used for recording a number or signal for identifying where the particular sample was taken from or the like.

Figure 7:
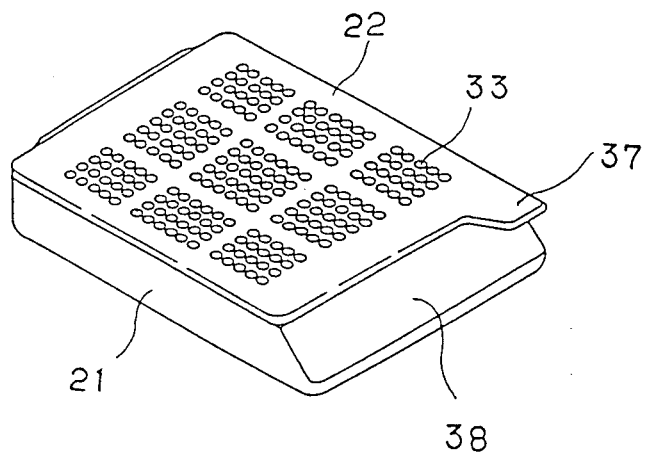
FIG. 7 is a schematic view showing a further different embodiment of the present invention.
Figure 8:
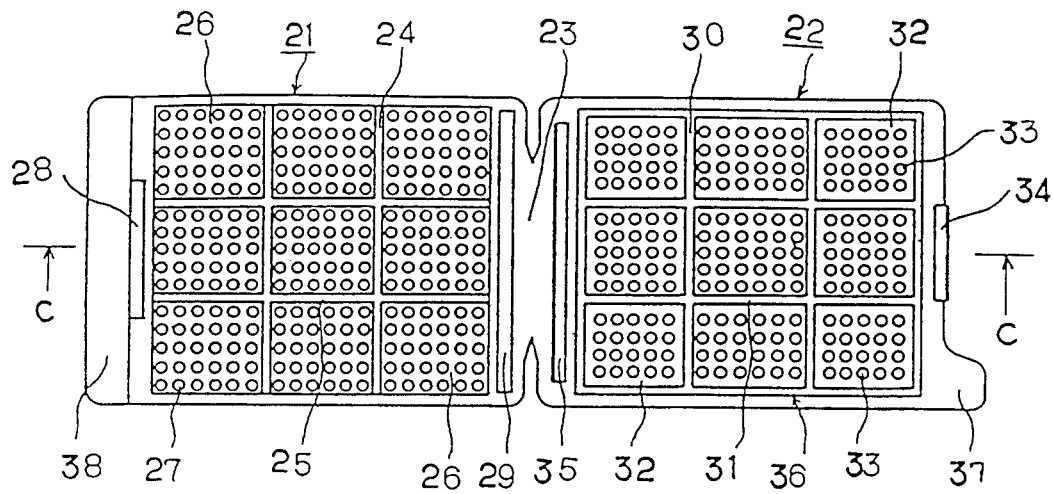
FIG. 8 is a plan view thereof with the lid opened.
Figure 9:
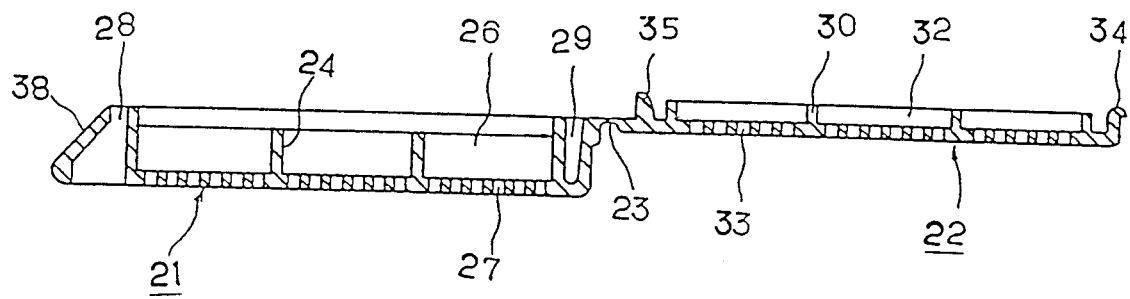
FIG. 9 is a sectional view taken along the line C—C in FIG. 8.

FIG. 7 is a schematic view of the cassette showing a still different embodiment of the invention, FIG. 8 is a plan view thereof with its lid opened, and FIG. 9 is a sectional view taken along the line C—C in FIG. 8.

Referring to these figures, the cassette of the present invention consists of a container proper (21) and a lid (22) and these are connected by a hinge (23). The aforementioned container proper (21) is partitioned by separators (24) and (25) longitudinally and horizontally to thus form a plurality (9 in the figure) of sample chambers (26) and in the bottom of the sample chambers (26) are made a large number of small through-holes (27). Near both ends of the container proper (21) there are provided sunken parts (28) and (29) and the container proper (21) is provided a recording space (38) for writing or otherwise recording the name, serial No. et cetera of the examinee.

Meanwhile, on the back of the aforementioned lid (22) there are provided the same number and size of a plurality (9 in the figure) of small spaces (32) formed by being partitioned, inside a surrounding rim (36), by separators (30) and (31) longitudinally and horizontally, to match the sample chambers (26) of the aforementioned container proper, and there are made a large number of small through-holes (33) inside these small spaces (32). Near both ends of the lid (22) there are provided projections (34) and (35), and there is further provided a holder (37).

The container proper (21) and the lid (22) as described above are mated when the hinge (23) is bent inward so that the projections (34) and (35) of the lid (22) fit in the sunken parts (28) and (29) of the container proper (21) and the separators (30) and (31) of the lid (22) fit in the separators (24) and (25) of the container proper (21) respectively for 9 independent and tightly sealed sample chambers to be formed thereby. To open the container, the holder (37) may be held with fingers and the lid (22) is lifted to break the aforementioned engagement.

An example is given below according to the cassette shown by FIGS. 1 to 4 to show how it is used. The sample is first placed into the sample chamber (4) of the container proper (1), the container is closed with the lid (2) and the sample is rinsed with water by means of the small through-holes (9) and (5) and then alcohol is passed through these holes for dehydrating the sample (part of the fat it contains is also removed at this stage). Then xylene is passed through for imparting to the sample affinity for liquid paraffin. Now, a stainless steel tray is filled with liquid paraffin, the desired sample is taken out of the sample chamber and placed on the liquid paraffin in the stainless steel tray. The cassette is placed on the supporting means of the stainless steel tray, and liquid paraffin is poured over the sample placed on the aforementioned liquid paraffin until the bottom of the cassette comes into contact with the liquid paraffin. After solidification of the liquid paraffin the tray is removed, and there results the so-called cassette block, which consists of the sample embedded in paraffin and the bottom of the cassette of the present invention, these forming a single body. The paraffin-embedded sample portion of this cassette block is then sliced by the use of a microtome to make preparations for microscopy.

The cassette for pathological tissue examination of the present invention has a good many advantages as enumerated below, being thus highly useful.

(1) A plurality of samples can be taken into plural, independent sample chambers, hence it is possible to treat simultaneously samples taken from a plurality of patients or samples taken from a single patient.

(2) A plurality of samples can be handled en bloc in a single treatment with alcohol or xylene.

(3) The cassette of the present invention can be used as it is also for making the cassette block using paraffin, being thus highly useful.

(4) By provision of the paraffin engaging and reinforcing means, secure engaging of the paraffin block with the bottom of the cassette is attainable and, moreover, a high reinforcing effect is attainable so that the wall thickness of the container proper can be reduced for smoother passage or permeation of alcohol or paraffin, and the reinforcing effect is also exhibited when slicing is done using the microtome.

(5) The lid and/or the container proper are/is provided with the recording part in which the necessary data can be written or otherwise recorded, hence primitive yet grave errors of mistaking the examinees and the like can be precluded. Also, by writing the number, signal and the like for identifying where each sample was taken from troubles such as mistaking the samples taken or mistaking the place a given sample was taken from can be avoided, the cassette of the invention thus contributing to improvement of the reliability of examination.

(6) Made of a synthetic resin, the cassette is safe from deformation even if it is subjected to a pretty large force.

(7) Compared with a conventional bag made of "mesh" cloth, taking-in and taking-out of samples is easier with the cassette of the present invention, this also featuring an improved permeability to alcohol or paraffin and better workability.

What is claimed is:

1. A cassette for pathological tissue examination consisting of a container proper and a lid, the lid being engagable with and detachable from the container proper, the container proper and the lid are made of a chemical-resistant synthetic resin, partition means associated with at least one of said container proper and said lid so that when said container proper and said lid are engaged the interior surface of the container proper, the interior surface of the lid and said partition means define a plurality of cylindrical sample chambers which are independent and separated from one another, the interior surface of the container proper defining each of said chambers having a plurality of small through-holes, the interior surface of the lid defining each of said chambers having a plurality of small through-holes, and a surface of at least one of said container proper and said lid having means for recording information for identifying pathological tissue.

2. A cassette in accordance with claim 1, wherein said container proper further includes a plurality of paraffin engaging and reinforcing members protruding from an external surface thereof.

3. A cassette in accordance with claim 1, wherein said partition means defines 3 to 9 sample chambers.

4. A cassette in accordance with claim 1, wherein said small through-holes have a diameter from 0.2 mm to 0.7 mm.

5. A cassette in accordance with claim 1, wherein said means for recording is located near each of said sample chambers.

6. A cassette for the pathological examination of a multiplicity of separate tissue samples consisting essentially of main container body means and lid means engagable therewith, both of which are made of chemical resistant synthetic resin, said main container body means having an upper surface, hinge means connecting said upper surface to said lid means in a movable manner, when said main container body means and said lid means are not engaged, said hinge means maintains said upper surface substantially coplanar with said lid means, said upper surface having chamber means defining a plurality of independent, individual, separate, substantially cylindrical, sample chambers therein, wherein each of said sample chambers has a lower surface containing a plurality of small through-holes therein, said lid means having a plurality of circular, projected rims equal in number to said sample chambers and dimensioned and positioned so as to engage said sample chambers in a sealable manner when said main container body means and said lid means are engaged, the area of said lid means encompassed by each of said circular rims having a plurality of small through-holes so as to provide flow communication between each of said sample chambers and said lid means, and a surface of at least one of said main container body means and said lid means, proximate to each of said sample chambers, having means for recording information related to the samples in each of said chambers.

7. A cassette as claimed in claim 6 further including a multiplicity of reinforcing means projecting from said upper surface in a direction away from said engaged lid means as well as away from said chambers; said reinforcing means also providing means for engaging liquid paraffin and for attaching a mold of said paraffin, after such has solidified, to a portion of said cassette outside said chambers.

* * * * *